US006350619B1

(12) United States Patent
Mercolino et al.

(10) Patent No.: US 6,350,619 B1
(45) Date of Patent: *Feb. 26, 2002

(54) CONTROL PARTICLES FOR CELL COUNTING AND INSTRUMENT LINEARITY

(75) Inventors: Thomas J. Mercolino, Stockton; Virendra O. Shah, Bernard Township, both of NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 08/206,917

(22) Filed: Mar. 4, 1994

Related U.S. Application Data

(63) Continuation of application No. 07/940,600, filed on Sep. 4, 1992, now abandoned.

(51) Int. Cl.[7] .............................................. G01N 33/533
(52) U.S. Cl. ....................... 436/518; 435/7.1; 435/7.24; 436/2; 436/8; 436/10; 436/16; 436/52; 436/56; 436/164; 436/172; 436/173; 436/805; 530/380
(58) Field of Search .............................. 435/7.21; 436/8, 436/10, 43, 63, 172, 548, 800; 250/459.1, 461.2; 530/380

(56) References Cited

U.S. PATENT DOCUMENTS

| 4,544,546 A | | 10/1985 | Wang et al. ................. 424/7.1 |
|---|---|---|---|
| 4,599,307 A | | 7/1986 | Saunders et al. .............. 435/34 |
| 4,704,891 A | | 11/1987 | Recktenwald et al. ........... 73/1 |
| 4,727,020 A | | 2/1988 | Recktenwald .................. 435/6 |
| 4,751,188 A | * | 6/1988 | Valet ........................... 436/63 |
| 4,867,908 A | * | 9/1989 | Recktenwald et al. ......... 436/8 |
| 4,876,190 A | * | 10/1989 | Recktenwald .................. 435/7 |
| 4,883,867 A | | 11/1989 | Lee et al. ...................... 536/28 |
| 4,937,198 A | | 6/1990 | Lee et al. ...................... 436/94 |
| 4,987,086 A | * | 1/1991 | Brosnan et al. ............. 436/501 |
| 5,047,321 A | * | 9/1991 | Loken et al. ................... 435/6 |
| 5,073,497 A | * | 12/1991 | Schwartz ...................... 436/10 |
| 5,073,498 A | | 12/1991 | Schwartz ....................... 435/7 |
| 5,084,394 A | * | 1/1992 | Vogt et al. .................... 436/10 |
| 5,093,234 A | * | 3/1992 | Schwartz ....................... 436/8 |

OTHER PUBLICATIONS

Stewart et al., Cytometry, 2:238–43 (1982).*

* cited by examiner

Primary Examiner—Bao-Thuy L. Nguyen
(74) Attorney, Agent, or Firm—David W. Highet

(57) ABSTRACT

This invention describes methods and kits for determining instrument linearity of a flow cytometer and is particularly useful as a control particle for use in conjunction with absolute cell counting methods. The particle used in the practice of this invention comprises a small fluorescent bead.

7 Claims, 2 Drawing Sheets

CONTROL PARTICLES FOR CELL COUNTING AND INSTRUMENT LINEARITY

This application is a continuation of application Ser. No. 07/940,600, filed Sep. 4, 1992 now abandoned.

FIELD OF THE INVENTION

This invention relates to the field of control particles products for flow cytometry, and more particularly relates to a method for providing checks on pipetting precision and instrument linearity. The invention is particularly useful in a method for the absolute counting of cells, such as reticulocytes and leukocytes and more particularly one or more subsets of leukocytes, in a cell sample.

BACKGROUND OF THE INVENTION

Flow cytometry comprises a well known methodology for identifying and distinguishing between different cell types in a non-homogeneous sample of cells. The sample may be drawn from a variety of sources such as blood, lymph, urine, or may be derived from suspensions of cells from solid tissues such as brain, kidney or liver. In the flow cytometer, cells are passed substantially one at a time through one or more sensing regions wherein each cell is illuminated by an energy source. The energy source generally comprises means that emits light of a single wavelength such as that provided by a laser (e.g., He/Ne or argon) or a mercury arc lamp with appropriate bandpass filters. Different sensing regions can include energy sources that emit light at different wavelengths.

In series with each sensing region, various light collection means, such as photomultiplier tubes, are used to gather light that is refracted by each cell (generally referred to as forward light scatter), light that is reflected orthogonal to the direction of the flow of the cells through a sensing region (generally referred to as orthogonal light scatter) and one or more light collection means to collect fluorescent light that may be emitted from the cell as it passes through a sensing region and is illuminated by the energy source. Light scatter is generally correlated with the physical characteristics of each cell.

Flow cytometers further comprise data recording and storage means, such as a computer, wherein separate channels record and store the light scatter and fluorescence data from each cell as it passes through a sensing region (i.e., all of the data collected for each cell comprise a "recorded event"). By plotting orthogonal light scatter versus forward light scatter in either real time or by reanalysis of the data after the events have been recorded, one can distinguish between and count, for example, the granulocytes, monocytes and lymphocytes in a population of leukocytes. By gating on only lymphocytes, for example, using light scatter and by the use of appropriate cell markers, such as monoclonal antibodies labelled with fluorochromes of different emission wavelength and/or nucleic acid dyes, one can further distinguish between and count cell types within the lymphocyte population (e.g., between $CD4^+$ and $CD8^+$ lymphocytes). U.S. Pat. Nos. 4,727,020, 4,704,891 and 4,599,307 describe the arrangement of the various components that comprise a flow cytometer and also the general principles of its use.

Because the accurate measurement of light either scattered by or emitted from a cell is critical to the operation of a flow cytometer, assuring that the instrument is properly setup is important to its daily operation and use. There are a number of products available to "setup" a flow cytometer. These products generally comprise polymeric microparticles which are labelled with one or more fluorescent dyes and which come in one or more sizes. The instrument operator has the ability once or more a day to "calibrate" or "align" the instrument using these particles to be sure that the instrument is functioning properly. U.S. Pat. Nos. 5,073,497, 5,073,498 and 5,084,394 describe such beads and methods of use in setting up a flow cytometer. Co-pending and commonly assigned U.S. Ser. No. 897,616 (filed Jun. 10, 1992) further describes the use of cells as control particles for staining and instrument calibration.

Apart from issues involving the use and operation of the instrument, there are other factors which can effect results gathered by means of flow cytometry. While it is possible using the above-described methods to count the number of cells in a sample and to distinguish between various cell populations, the number of cells counted will be relative (i.e., it will not give an absolute count for a specific volume of blood, for example). Generally, these methods require that red blood cells be substantially removed from the sample. One reason is because the light scatter of the red blood cells and leukocytes is substantially overlapping making their differentiation based on light scatter alone difficult. Another reason is that in order to count leukocytes in a more rapid manner the number of red blood cells must be reduced because the number of red blood cells to leukocytes is approximately 1,000 to 1. Accordingly, practitioners in the field routinely lyse whole blood or separate out the blood cell components by density dependent centrifugation.

In addition to the step required for whole blood separation, other steps are routinely involved. For example, before or after lyses cell markers generally are added. Unbound markers, then, are routinely washed from the cells. After that step, a fixative is added. Finally, cells in solution are run on a flow cytometer. In some flow cytometers, all of the solution containing cells is delivered to the cytometer for analysis. In other flow cytometers, only a measured amount of solution is delivered.

While lysis and washing steps are routine, there are now methods and procedures that do not involve washing. These so-called "no-wash" methods involve the addition of immunofluorescence markers and fixatives without washing steps. Co-pending and commonly assigned U.S. Ser. No. 846,316 (filed Mar. 5, 1992) is directed to one such method.

Regardless of the method or instrument used, any step in which the sample of cells is physically manipulated introduces not only the possibility for error, but also the potential for loss of cells from the sample. In addition, each step increases the risk to the technician of being exposed to contaminated blood.

Thus, in each of the presently described systems, there are one or more obstacles that limit ease in assuring instrument accuracy. These obstacles are not overcome by the mere addition of a reference particle, as described in U.S. Pat. No. 4,110,604, with flow cytometry or the occasional calibration of the instrument with control particles. Several drawbacks remain.

A major drawback to the use of flow cytometers is that unless the fluorescence channels and optical alignment of each flow cytometer is calibrated to read the same, there is no assurance as to the source of variation in a sample. It is likely that one instrument will give different readings on the same sample on different days if it was aligned and/or calibrated differently each day. Similarly, there is no assurance that any two instruments will provide the same results even if properly set up Accordingly, while flow cytometry provides a better measure of identifying and distinguishing between cells in a sample, its present use as a clinical instrument may be diminished by the limitations in set up and operation if not properly performed. What is required is a single system or method that will allow one to accurately count cells in a sample and/or be assured that the results from one instrument are consistent from sample to sample as well as consistent with results obtained from other instruments.

Even through the resolution of some of these problems through the methods and kits described in co-pending and commonly assigned U.S. Ser. No. 570,569 (filed Aug. 7, 1990), additional issues remain. For example, the use of a single reference particle will provide a means to perform absolute counts in a cell sample. The addition of such particles, however, does not assure that the technician handling the samples or the equipment used to handle the samples are accurate. Sample error introduced through the pipetting step can be a source of significant variation which cannot be otherwise accounted for. Similarly, the use of a single reference particle may not assure that the flow cytometer is accurately counting the particles, and thus, the cells. If the particle count is not accurate, the cell count cannot be accurate.

The present invention overcomes all of these obstacles and provides a one step test for absolute counting of one or more specific populations of cells in an unlysed whole blood sample. The present invention further provides a check on pipetting accuracy and provides a check on instrument linearity.

SUMMARY OF THE INVENTION

This invention, therefore, relates to a method and kit comprising control reagents for conventional (i.e., non-absolute) cell counting. In this method, a test sample is split into more than one aliquot, preferably two, more preferably four, and each aliquot is added to a separate tube. Each tube may contain one or more cell markers or the markers may be added as a separate step. To each tube is added a known concentration of microparticles. The concentration of microparticles in each tube will differ. Each tube then is analyzed by means of flow cytometry and the number of microparticles and cells per tube is counted. The result from counting should be linear if instrument linearity is correct. In the instance where two or more cell markers are being used to identify two or more subsets of cells, it is preferable to use at least four tubes and to add one cell marker to two tubes and the other cell marker to the two other tubes. In this instance, if the instrument is functioning properly, the coefficients of variation between tubes containing the same marker should be minimal.

The invention has particular utility in a method and kit for the absolute counting of one or more populations of cells in a sample. The preferred means for counting such cells comprises a flow cytometer. In this embodiment of the method, a test sample is added to a tube. The tube may contain a diluent. The diluent may comprise a mixture of a fixative, one or more cell markers and a known amount of a first microparticle. The first microparticle is fluorescent and the fluorescence is distinguishable from the fluorescence emitted by the cell marker(s). To this mixture, a known amount of a second fluorescent microparticle is added. The fluorescence of the second microparticle is distinguishable from the fluorescence emitted by the cell marker(s) and the first microparticle. The sample then is vortexed, incubated, vortexed again and run on a flow cytometer having one or more fluorescence channels.

In an alternative embodiment, the diluent may comprise only the cell markers. In that instance, the fixative and first microparticles are added separately. In another embodiment, the diluent may comprise the cell markers and first microparticles. The fixative is added separately. The timing of the addition of these various components is not critical to the practice of the invention.

Fluorescence data is recorded and stored for each event. A fluorescence trigger is set for one fluorescence channel so as to include essentially all of the microparticles and cells to be counted. The number of microparticles then is counted by analyzing the recorded events.

Counting the number of cells in the sample, the number of first microparticles and by knowing the amount of first microparticles added per unit volume, the number of cells in each population can be absolutely counted. Counting the number of second microparticles and the number of first microparticles in the sample permits a check on pipetting accuracy and instrument linearity.

A kit useful in the practice of this invention comprises the following items: a sample tube and a diluent wherein the diluent comprises a mixture of one or more cell markers and a known amount of a first microparticle. The kit also will contain two or more containers having different concentrations of a second microparticle. The diluent may be packaged in the tube. In the tube, the diluent may be liquid or may be dried by methods known to those skilled in the art such as lyophilization. Drying may be performed in the presence of a stabilization agent such as trehalose. In the dried format, the "diluent" will be return to solution upon addition of the liquid sample such as blood. In any embodiment, the diluent may be separately contained or may be broken up into its several components each of which may be separately contained. In these alternatives, the diluent may be added to the sample tube before or after the sample is added to the tube.

Another kit useful in the practice of this invention comprises two or more tubes and two or more containers each container having a different amount of a fluorescent microparticle contained therein.

DETAILED DESCRIPTION

Figure 1A:
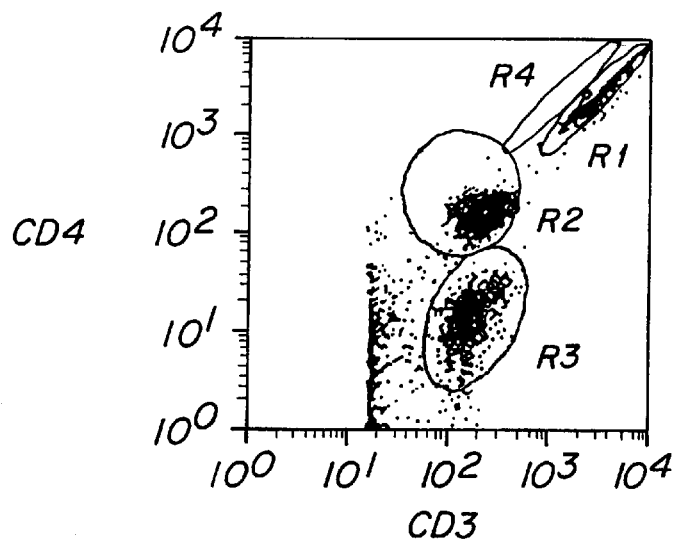
FIG. 1 comprises four dot plots of log fluorescence 2 versus log fluorescence 1 for recorded events exceeding a first fluorescence trigger on the log fluorescence 1 axis from unlysed whole blood cells split into four aliquots and stained with a diluent containing in (A) and (B) anti-CD3(PE) and anti-CD4(PE/CY5) and in (C) and (D) anti-CD3(PE) and anti-CD8(PE/CY5). In all four tubes, the diluent contained the same amount of a first fluorescent microparticle. In (A), 0 second microparticles per $\mu$l were added; in (C), 56 second microparticles per $\mu$l were added; in (B), 278 second microparticles per $\mu$l were added; and in (D), 1115 second microparticles per $\mu$l were added.

The invention comprises methods and kits for determining instrument linearity and pipetting accuracy and is particularly useful as part of a method for determining the absolute count for one or more populations of cells in a sample, preferably, by flow cytometry. In either instance, the sample may be derived from any tissue source or cell line, but generally is selected from the group consisting of whole blood, lymph, spinal fluid, urine and bone marrow. Unlysed whole blood is preferred as a source of cells for determining instrument linearity.

The populations of cells that can be counted in a sample comprise platelets, red blood cells, white blood cells and subsets and precursors of each. One preferred population of red blood cells comprise reticulocytes. The preferred subsets of leukocytes comprise lymphocytes, monocytes and granulocytes. In one preferred embodiment, lymphocyte subsets are particularly important and more preferred is the counting of $CD4^+/CD3^+$ and $CD8^+/CD3^+$ T lymphocytes in an unlysed whole blood sample. It will be appreciated that this invention is applicable to counting any population of cells (e.g., $CD34^+$ stem cells) as well as to any number of populations of cells. For example, in order to count both the number of $CD4^+$ and $CD8^+$ T lymphocytes in a sample, one would use anti-CD4 and anti-CD8 antibodies. In such an instance, it is preferable to use anti-CD3 antibodies as well count only those CD4 and CD8 cells that are lymphocytes. In another example, to calculate a three part white blood cell differential, one could use anti-CD45, anti-CD14 and anti-CD15 antibodies. In still another example, to calculate the absolute number of T lymphocytes and/or B lymphocytes, one could use anti-CD3 and/or anti-CD19 (or anti-CD20) antibodies to count T cells or B cells respectively. Any population that can be identified by a single cell marker can be counted alone or can be counted with other populations in the same sample.

Cell markers useful in the practice of this invention comprise immunofluorescence markers and other fluorescence tagging agents which will specifically label one or more populations of cells. As set forth above, immunofluorescence markers comprise antibodies bound to fluorochromes. Monoclonal antibodies are preferred. Examples of fluorescence tagging agents include nucleic acid dyes, such as those described in U.S. Pat Nos. 4,544,546, 4,883,867 and 4,937,198, and such dyes as propidium iodide, acridine orange, thiazole orange, thioflavin T and 7-aminoactinomycin D. A preferred nucleic acid dye described generally by formula I of U.S. Pat. No. 4,544,546 having a quinoline nucleus is presently marketed as a laser dye under the tradename LDS-751 (Exciton).

Fluorochromes useful in the practice of this invention may be excitable at the same wavelength of light. Dyes having these properties include the phycobiliproteins (especially phycoerythrin "PE"), fluorescein derivatives (such as fluorescein isothiocyanate "FITC"), peridinin chlorophyll protein complex (such as described in U.S. Pat. No. 4,876,190 "PerCp"), coumarin derivatives (such as aminomethyl coumarin), pthalocyanine dyes (such as Ultralite dyes (Ultradiagnostics)), rhodamine derivatives (such as tetramethyl rhodamine or Texas Red (Molecular Probes)) and carbocyanines (such as CY3 and CY5 (Biological Detection Systems)). Tandem conjugates formed between two of the dyes set forth above also may be useful within the practice of this invention. See U.S. Pat. No. 4,542,104.

When more than one population of cells is to be counted, more than one cell marker may be used (each being specific for a different population); however, the fluorescence of each marker must have emission wavelengths that are distinguishable not only from each other but also from the microparticles used. When only one immunofluorescence marker is used, PE is preferred as the fluorochrome. When two or more immunofluorescence markers are used, PE and a tandem conjugate formed between PE and CY5 is preferred.

The microparticle used in the practice of this invention should have certain properties. First, it should be small (i.e., between 0.2 $\mu$m and 20 $\mu$m, with 4 $\mu$m preferred) so as to stay suspended in the mixture and not settle any faster than the cells in the sample. Second, it should be made of a material that avoids clumping or aggregation. Polystyrene is preferred. Third, it should be fluorescent. Fluorescence can be achieved by selecting the material that comprises the microparticle to be autofluorescent or it can be made fluorescent by being tagged with one or more fluorescent dyes to appear autofluorescent. A combination of red and blue emitting dyes are preferred.

The fluorescence of the microparticles must be such that it is sufficiently greater than noise from background so as to be distinguishable. When used with one or more cell markers and/or with another microparticle (i.e., first microparticle), it also must be distinguishable from the fluorescence emitted by such marker(s), and/or from the fluorescence emitted by another microparticle. Three standard deviation difference between that fluorescence and the microparticle fluorescence is sufficient. Microparticles having these properties may be selected from the group consisting of fixed chicken red blood cells, coumarin beads, liposomes containing a fluorescent dye, fluorescein beads, rhodamine beads, fixed fluorescent cells, fluorescent cell nuclei, microorganisms and other beads tagged with a fluorescent dye. Polystyrene microparticles tagged with red and blue emitting dyes are preferred.

The concentration range of the microparticle should be sufficient to demonstrate linearity and pipetting accuracy. The lower endpoint of the range is preferably 0 particles per unit volume while the upper endpoint of the range should be at or near the concentration of cells in a sample to be counted. Generally, two different concentrations of particles is preferred; three different concentrations is more preferred; and four different concentrations is most preferred. When more than two concentrations are used, it is preferred that at least two of concentrations be at or near the endpoints.

In one embodiment of the invention, therefore, identical volumes of each of the different concentrations of microparticles are added to different tubes containing equal volumes of a sample. Thus, in the most preferred embodiment, one tube will contain 0 particles per $\mu$l, one tube will contain a concentration of particles at or near the number of cells to be counted in a sample (e.g., 1000 per $\mu$l), and each of the two remaining tubes will contain different concentrations in between (e.g., 55 particles per $\mu$l and 275 particles per $\mu$l).

The flow cytometer should be equipped with one or more fluorescence detectors (arbitrarily referred to as fluorescence channels 1 and 2 or "FL1" and "FL2" etc.) and with data recording and analysis means, such means generally comprising a computer. Each of the tubes then are run through the flow cytometer. Fluorescence and scatter data for each event is recorded. A fluorescence trigger is set such that essentially all the microparticles to be counted meet or exceed the trigger level. In the preferred embodiment, the trigger is set to include at least 99%, and preferably 99.99%, of all microparticles to be counted. The data is recorded and an analysis of the data is made to determine if the instrument is counting the particles in the different tubes in a linear manner and if pipetting is accurate. The data may be analyzed by simple statistical analysis such as standard regression analysis.

In another embodiment of the invention, the particles are added to two or more aliquots of a test sample containing cells. Where only a single cell marker is being used, two different concentrations of the particles may be used although, again, four is preferred for statistical reasons. Where two or more cell markers are being used, it is preferable to use at least four different concentrations of particles.

The following example describes each embodiment of the invention in more detail and makes use of the methods described in U.S. Serial No. 570,569.

Unlysed whole blood was divided into ten replicates of four aliquots each. In the four aliquots, two ((A) and (B)) contained a diluent comprising anti-CD3(PE/CY5) and anti-CD4(PE) and the other two tubes ((C) and(D)) contained anti-CD3(PE/CY5) and anti-CD8(PE). All four tubes contained a first microparticle consisting of a polystyrene microsphere containing orange emitting dyes at a concentration of 150 per µl.

A second microparticle consisting of a polystyrene bead containing red and blues dyes was set used to establish a range of concentrations. The concentrations selected were 0, 56, 278 and 1115 particles per µl. 50 µl of a concentration was added to each of the four aliquots: 0 to (A); 278 to (B); 56 to (C); and 1115 to (D). The tubes were vortexed, a fixative was added and each tube was analyzed on a FACScan brand flow cytometer (BDIS). The instrument was equipped with LYSIS II software (BDIS).

Figure 1B:
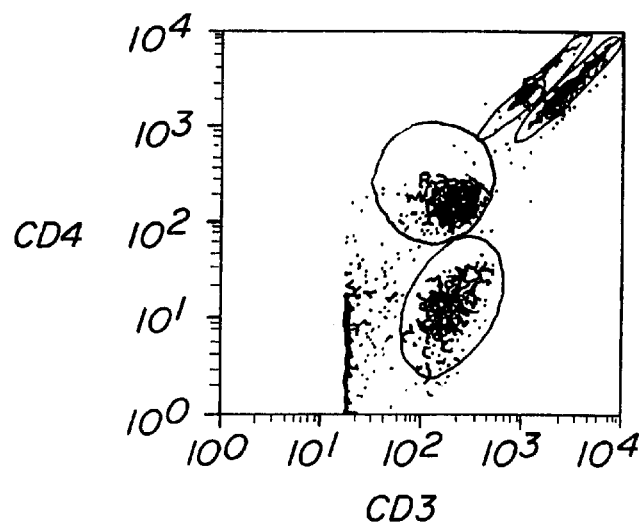
Figure 1C:
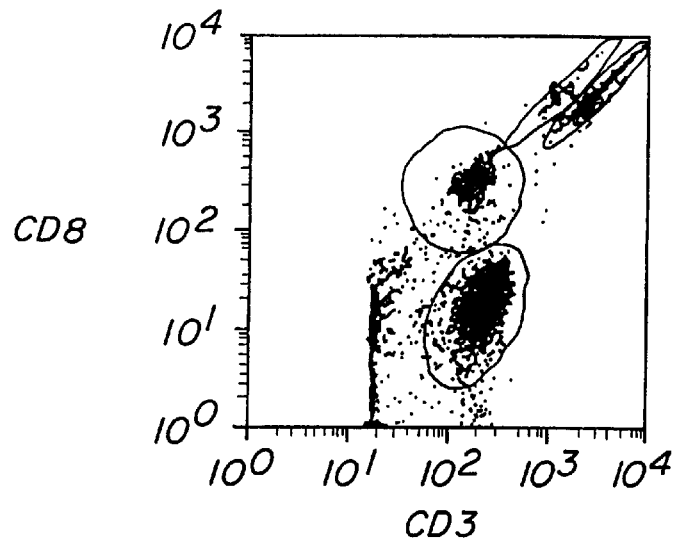
Figure 1D:
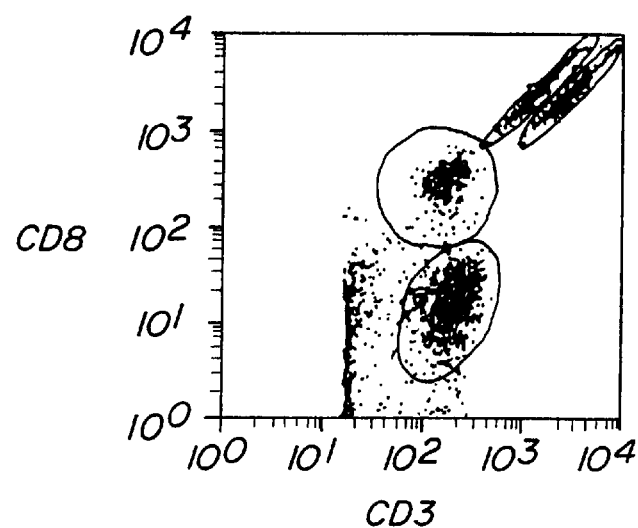

Referring to FIG. 1, the results of the analysis are shown. In (A), the area circled and labelled "R3" contains those cells that are CD3+ but not CD4+. "R2" contains those cells that are CD3+ and CD4+. "R1" contains the first microparticles and "R4" contains the second microparticles. The unlabelled circles in (B), (C) and (D) have same meanings as in (A) except that CD4 is replaced by CD8 in (C) and (D).

Comparing (A) with (B), it is apparent that the only visual difference in these plots is in the contents of the circle labelled R4 because the number of CD4 and CD3 cells should not vary between the tubes nor should the number of first microparticles. The same is true when (C) and (D) are compared. When all four aliquots are compared, there are no visual differences between each of the R1 areas nor between each of the R3 areas because each should contain the same number of CD3 cells and first microparticles if the instrument is properly aligned and pipetting of the reagents was accurate. Table I summarizes the actual counts for CD4/CD8, CD3 and second microparticle from each replicate.

TABLE I

| TUBE | REP# | CD4/CD8 COUNT | CD3 COUNT | 2ND PARTICLE COUNT | 2ND PARTICLE INPUT |
|---|---|---|---|---|---|
| A | 1 | 700 | 999 | 0 | 0 |
| A | 2 | 696 | 1011 | 0 | 0 |
| A | 3 | 670 | 968 | 3 | 0 |
| A | 4 | 700 | 1007 | 1 | 0 |
| A | 5 | 668 | 966 | 0 | 0 |
| A | 6 | 663 | 980 | 1 | 0 |
| A | 7 | 684 | 969 | 1 | 0 |
| A | 8 | 684 | 998 | 1 | 0 |
| A | 9 | 676 | 977 | 1 | 0 |
| A | 10 | 691 | 992 | 0 | 0 |
| B | 1 | 674 | 960 | 266 | 278 |
| B | 2 | 689 | 990 | 287 | 278 |
| B | 3 | 667 | 957 | 271 | 278 |
| B | 4 | 694 | 985 | 274 | 278 |
| B | 5 | 685 | 984 | 288 | 278 |
| B | 6 | 644 | 918 | 282 | 278 |
| B | 7 | 662 | 963 | 291 | 278 |
| B | 8 | 659 | 951 | 269 | 278 |
| B | 9 | 667 | 960 | 264 | 278 |
| B | 10 | 698 | 1011 | 280 | 278 |
| C | 1 | 245 | 989 | 62 | 56 |
| C | 2 | 239 | 958 | 59 | 56 |
| C | 3 | 252 | 953 | 52 | 56 |
| C | 4 | 241 | 922 | 54 | 56 |
| C | 5 | 255 | 1015 | 57 | 56 |

TABLE I-continued

| TUBE | REP# | CD4/CD8 COUNT | CD3 COUNT | 2ND PARTICLE COUNT | 2ND PARTICLE INPUT |
|---|---|---|---|---|---|
| C | 6 | 234 | 943 | 54 | 56 |
| C | 7 | 255 | 986 | 62 | 56 |
| C | 8 | 252 | 1006 | 55 | 56 |
| C | 9 | 257 | 1014 | 68 | 56 |
| C | 10 | 248 | 942 | 60 | 56 |
| D | 1 | 248 | 967 | 1175 | 1115 |
| D | 2 | 248 | 959 | 1101 | 1115 |
| D | 3 | 251 | 993 | 1087 | 1115 |
| D | 4 | 241 | 932 | 1085 | 1115 |
| D | 5 | 254 | 996 | 1181 | 1115 |
| D | 6 | 229 | 908 | 1073 | 1115 |
| D | 7 | 247 | 945 | 1114 | 1115 |
| D | 8 | 234 | 916 | 1108 | 1115 |
| D | 9 | 250 | 951 | 1114 | 1115 |
| D | 10 | 238 | 947 | 1114 | 1115 |

Taking the data tabulated in Table I, the mean, standard deviation ("S.D") and coefficient of variation ("CV%") were calculated for CD4/CD8, CD3 and second microparticle in each of tubes (A), (B), (C) and (D), for all CD4 cells (i.e., (A) and (B)), for all CD8 cells (i.e., (C) and (D)), and for all CD3 cells (i.e., (A), (B), (C) and (D)). The results are summarized in Table II.

TABLE II

| TUBE | | CD4/CD8 | CD3 | 2ND PARTICLE |
|---|---|---|---|---|
| A | Mean | 683 | 987 | 1 |
|   | S.D. | 13 | 16 | 1 |
|   | CV % | 1.9 | 1.6 | 96.3 |
| B | Mean | 674 | 967 | 277 |
|   | S.D. | 16 | 24 | 9 |
|   | CV % | 2.4 | 2.5 | 3.3 |
| C | Mean | 247 | 973 | 58 |
|   | S.D. | 8 | 32 | 5 |
|   | CV % | 3.1 | 3.3 | 7.8 |
| D | Mean | 244 | 952 | 1115 |
|   | S.D. | 8 | 28 | 34 |
|   | CV % | 3.2 | 2.9 | 3.1 |
| CD4 | Mean | 679 | 977 | N.A. |
|   | S.D. | 15 | 23 | |
|   | CV % | 2.3 | 2.3 | |
| CD8 | Mean | 245 | 962 | N.A. |
|   | S.D. | 8 | 32 | |
|   | CV % | 3.2 | 3.3 | |
| CD3 | Mean | 970 | N.A. | N.A. |
|   | S.D. | 28 | | |
|   | CV % | 2.9 | | |

As expected, CD4 and CD8 absolute counts are consistent between replicates within a tube. The coefficient of variation of all forty total CD3 determinations was 2.9%. By having four determinations made, the CD3 count can be used to detect pipetting imprecisions.

For the linearity determinations, linear regression analysis yielded an $R^2$ value of 0.998 with a slope of 0.999±0.006. Thus, any $R^2$ value which differed significantly from 1 would detect a deviation from linearity. Similarly, pipetting accuracy would be reflected in an altered regression slope.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed is:

1. In a method for absolute counting of cells in a sample wherein the sample comprises cells mixed with one or more cell markers having an emission spectra and a known number of a first fluorescent microparticle having an emission spectra, wherein the emission spectra of the cell markers and the first microparticle are distinguishable, a method comprising the steps of:

(a) separating the sample into at least two aliquots;

(b) adding equal volumes of mixtures containing known concentrations of a second fluorescent microparticles in a diluent to each of the aliquots, wherein the concentration of second fluorescent microparticles added to each aliquot differs and wherein the second microparticle has an emission spectra which is distinguishable from the emission spectra of the first microparticle and cell markers;

(c) counting the number of fluorescent cells, the number of first microparticles, and the number of second microparticles in each aliquot by means of flow cytometry; and (d) performing statistical analysis on the number of cells counted, the number of first microparticles counted and the number of second microparticles counted in all aliquots to determine linearity.

2. The method of claim 1 wherein the number of aliquots is four.

3. The method of claim 1 wherein the cell markers comprise fluorescently labelled monoclonal antibodies.

4. The method of claim 3 wherein the cell markers comprise fluorescently labelled anti-CD4, anti-CD8 and anti-CD3 monoclonal antibodies.

5. The method of claim 3 wherein the fluorescent dyes are selected from the group consisting of phycobiliproteins, fluorescein derivatives, peridinin chlorophyll protein complex, coumarin derivatives, pthalocyanine dyes, rhodamine derivatives, carbocyanines and tandem conjugates formed between two of the dyes set forth herein.

6. The method of claim 5 wherein the dye is a phycobiliprotein.

7. The method of claim 5 wherein the dye is a carbocyanine.

* * * * *